(12) United States Patent
Tomita et al.

(10) Patent No.: US 7,337,654 B2
(45) Date of Patent: Mar. 4, 2008

(54) METHOD OF FORMING A NEEDLE FOR AUTO-SAMPLER

(75) Inventors: Masami Tomita, Kyoto (JP); Yoshiaki Maeda, Kyoto (JP)

(73) Assignee: Shimadzu Corporation, Kyoto, Kyoto (JP)

( * ) Notice: Subject to any disclaimer, the term of this patent is extended or adjusted under 35 U.S.C. 154(b) by 0 days.

(21) Appl. No.: 11/648,640

(22) Filed: Jan. 3, 2007

(65) Prior Publication Data

US 2007/0130748 A1 Jun. 14, 2007

Related U.S. Application Data

(63) Continuation of application No. 11/082,908, filed on Mar. 18, 2005, now abandoned.

(30) Foreign Application Priority Data

Mar. 30, 2004 (JP) .............................. 2004-100328

(51) Int. Cl.
*G01N 1/12* (2006.01)

(52) U.S. Cl. .................................... 73/61.56; 73/61.55
(58) Field of Classification Search ............... 73/61.55, 73/61.56

See application file for complete search history.

(56) References Cited

U.S. PATENT DOCUMENTS

2002/0102185 A1* 8/2002 Tatsumi ...................... 422/100
2003/0189053 A1* 10/2003 Felbaum ...................... 220/582
2006/0049056 A1* 3/2006 Wang et al. ................. 205/123

* cited by examiner

*Primary Examiner*—Daniel S. Larkin
*Assistant Examiner*—Paul M West
(74) *Attorney, Agent, or Firm*—Manabu Kanesaka

(57) ABSTRACT

In a method of forming a needle for an auto-sampler successively collecting liquid samples from plural sample containers, a parent material forming the needle is coated with a coating material having a chemical activity small than that of the needle. Then, the coated parent material is polished so that the surface has an average roughness of 10 to 20 nm.

8 Claims, 4 Drawing Sheets

US 7,337,654 B2

METHOD OF FORMING A NEEDLE FOR AUTO-SAMPLER

CROSS-REFERENCE TO RELATED APPLICATION

This is a continuation application of Ser. No. 11/082,908 filed on Mar. 18, 2005 now abandoned.

BACKGROUND OF THE INVENTION AND RELATED ART STATEMENT

The present invention relates to a method of forming a needle for an auto-sampler of an analytical device such as a liquid chromatograph for analyzing liquid as an analytical subject.

In an auto-sampler, it is necessary to clean a needle after collecting a certain sample. The cleaning process is important in order to prevent a previous sample from mixing into a next sample (cross-contamination). The needle is typically made of stainless steel, i.e., an alloy consisting mainly of iron. Accordingly, iron is microscopically exposed on a surface of the needle, and a certain ingredient in a sample may preferably adhere to iron due to a chemical property of iron. For example, an alkaline substance easily adheres chemically due to a hydroxyl group thereof attracted to iron on a surface of stainless steel. Once an ingredient of a sample adheres chemically, it is difficult to remove the ingredient even through physical cleaning with a cleanser of organic solvent. A trace amount of the ingredient may adhere to a surface of the needle even after cleaning. Accordingly, it is possible that the ingredient mixes into a next sample when the next sample is collected, thereby causing cross-contamination.

In order to prevent the cross-contamination, the needle is coated with a layer of precious metal, synthetic resin, quartz, or the like, thereby preventing the chemical adsorption phenomenon (see Patent Document 1).

Patent Document 1; Japanese Patent Publication (Kokai) No. 2002-228668.

Even when the needle is coated with metal or resin for preventing the chemical adsorption phenomenon, it is possible that the needle has a rough surface depending on a process of metal plating or resin coating. As a result, small bumps and cavities may be formed on the surface of the needle. In this case, liquid may penetrate into a pleat of the bump or cavity and remain on the surface of the needle, thereby causing cross-contamination.

In view of the problems described above, an object of the present invention is to provide a method of forming a needle for an auto-sampler with a coated surface and capable of preventing cross-contamination.

Further objects and advantages of the invention will be apparent from the following description of the invention.

SUMMARY OF THE INVENTION

In order to attain the objects described above, according to the present invention, an auto-sampler successively collects liquid samples from plural sample containers through a metallic needle. A surface of the needle is coated with a coating material having a chemical activity smaller than that of a parent metal material of the needle, and the coated surface is polished to have an average roughness of 10 to 20 nm. The coating material on the needle surface may include a precious metal or synthetic resin plated or deposited on the parent metal material, or a quartz thin film formed by chemical vapor deposition on the parent metal material. The coating film on the needle is polished with a mechanical or chemical polishing method.

In the invention, the needle is coated with the coating material having a chemical activity smaller than that of the parent metal material. The coating film is polished to have a small surface roughness. Accordingly, it is possible to prevent cross-contamination caused by liquid remaining in bumps and cavities on the surface. A liquid chromatograph may use the needle of the present invention, so that it is possible to eliminate interference due to cross-contamination, thereby obtaining high sensitivity of analysis.

BRIEF DESCRIPTION OF THE DRAWINGS

FIGS. 1(A) and 1(B) are sectional views showing needles of an auto-sampler according to an embodiment of the present invention, wherein FIG. 1(A) is a needle having a surface coated with platinum plating and polished, and FIG. 1(B) is a needle having a surface coated with a synthetic resin and polished;

DETAILED DESCRIPTION OF PREFERRED EMBODIMENTS

Figure 2:
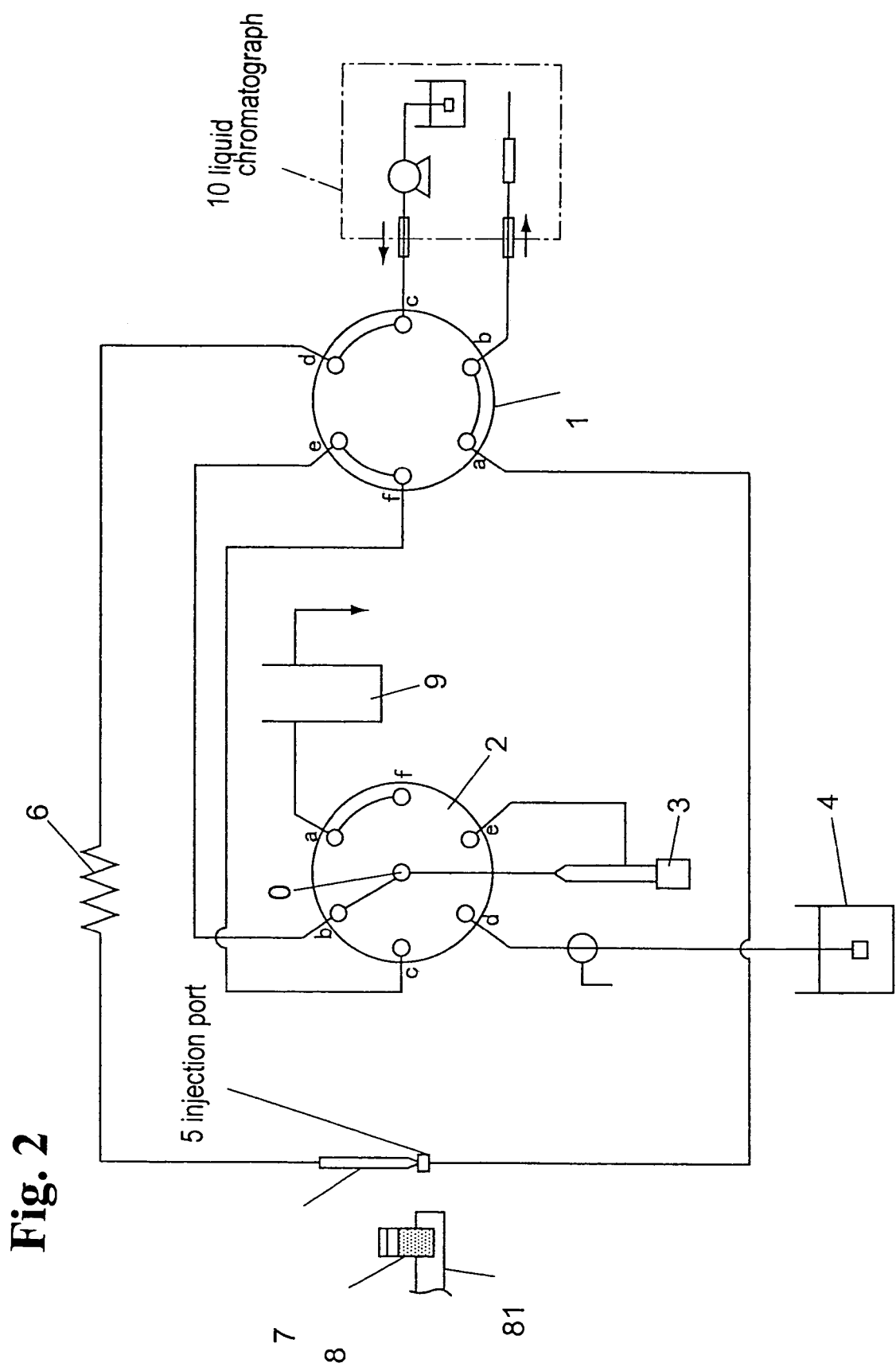
FIG. 2 is a schematic diagram showing an auto-sampler of a liquid chromatograph according to an embodiment of the present invention.

Hereunder, embodiments of the present invention will be explained with reference to the accompanying drawings. FIG. 2 is a schematic diagram showing an auto-sampler of a liquid chromatograph according to an embodiment of the present invention. In the drawing, reference numeral 3 denotes a plunger moving reciprocally with a mechanical force. Sample solutions to be analyzed are sealed in plural vials (small-capacity sample bottles) 8 in advance, and are placed on a rack 81. A needle 7 for collecting the samples from the vials 8 is connected to an injector valve 1 with a flexible loop tube 6 (loop). The needle 7 is also supported by a drive mechanism (not shown), and is capable of moving freely between the vials 8, a cleaning port 9, and an injection port 5 in accordance with a program.

A valve 2 is a rotary six-position valve for switching the flow channels of the liquids to be attracted and ejected by the plunger 3. Reference numeral 4 denotes a bottle of cleaning solution. The injector valve 1 is connected through piping to a liquid chromatograph apparatus 10, and introduces a sample solution into mobile phase liquid.

A process of sample injection using the analytical auto-sampler will be explained next.

(1) The injector valve 1 is adjusted so that ports e to d communicate. The valve 2 is adjusted so that ports 0 to b communicate as shown in the drawing. The needle 7 is inserted into the vial 8, and the plunger 3 is pulled to collect a prescribed quantity of the sample solution. The sample solution stays inside the loop 6, and does not reach the valve 2 or the plunger 3.

(2) The needle 7 is removed from the vial 8, and moved to the injection port 5.

(3) The injector valve 1 is operated into a state shown in the figure. The sample inside the loop 6 is introduced into the flow channel of the mobile phase liquid, thereby initiating liquid chromatographic analysis.

(4) After the needle 7 is cleaned and moved to the vial 8 containing the sample to be analyzed next, steps (1)-(3) above are repeated.

Figure 1A:
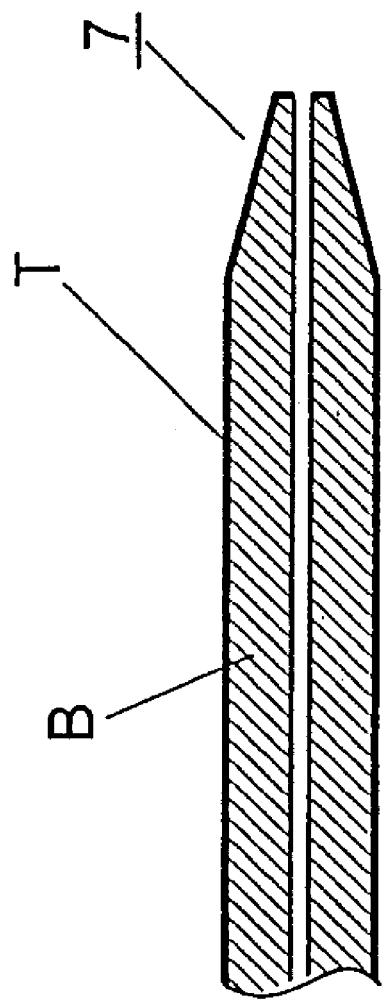
Figure 1B:
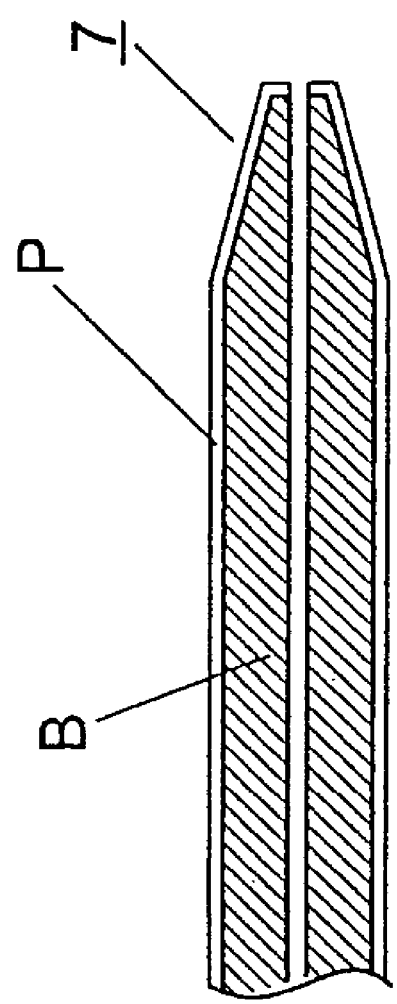

FIGS. 1(A) and 1(B) are sectional views showing needles of an auto-sampler according to an embodiment of the present invention. FIG. 1(A) is a needle having a surface coated with platinum plating and polished, and FIG. 1(B) is a needle having a surface coated with a synthetic resin and polished.

The needle 7 shown in FIG. 1(A), for example, is a flat-head type needle having an outer diameter of 1.2 mm, an inner diameter of 0.5 mm, and a flat tip with a diameter of 0.65 mm. A parent material B is made of stainless steel, and has a surface coated with a platinum plating layer T having a thickness of several μm to several tens of μm. The surface after plating is polished so that the surface roughness becomes smaller. An average roughness Ra is 10.14 nm, and an average roughness Rtm of 10 points of maximum roughness is 101.43 nm. The polishing process may be a mechanical process using abrasive grains, or a chemical polishing of treating the needle chemically.

In the mechanical polishing method, the needle may be polished by hand with abrasive grains affixed to a polishing cloth. In the chemical polishing method, the needle is immersed in an acid-based liquid to be chemically dissolved.

In the needle 7 shown in FIG. 1(B), instead of the metal plating, the parent material B is coated with a coating film P (thickness about 300 μm) of a synthetic resin, i.e., PEEK (polyetheretherketone) having excellent chemical resistance and mechanical strength. As the method of coating, a powder coating method can be applied. Considering a thickness of the synthetic resin coating film P, the parent material B must be made considerably thin in advance. PEEK is an organic material, and exhibits substantially no chemical adsorption. Further, because of excellent chemical resistance against various chemicals used in liquid chromatographs, PEEK is used as a piping material for liquid chromatographs, and is suitable for coating the needle 7 of the auto-sampler of liquid chromatograph. In this case, the needle is polished by hand with abrasive grains affixed to a polishing cloth, and the surface roughness same as that in the embodiment shown in FIG. 1(A) is obtained.

Figure 3A:
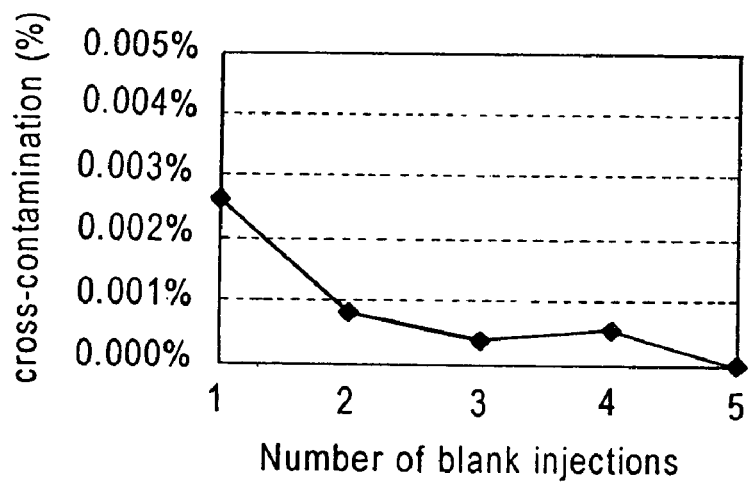
FIGS. 3(A) to 3(C) are charts showing an effect of reducing cross-contamination in a case of a needle having a surface coated with platinum plating.
Figure 3B:
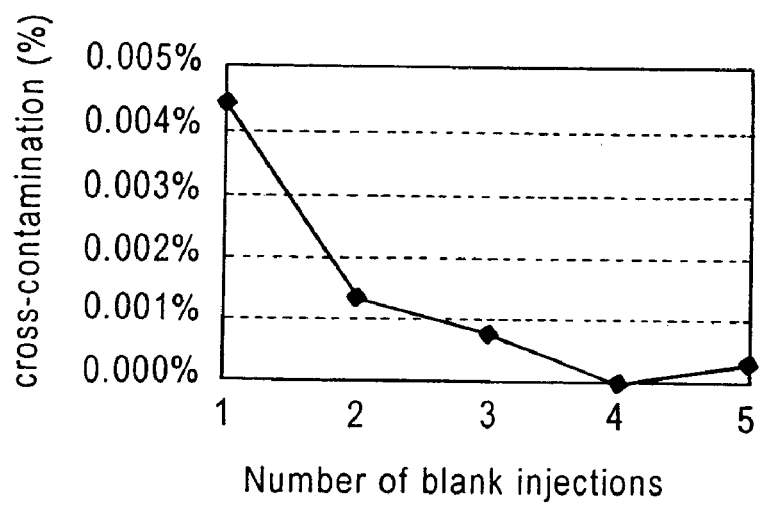
Figure 3C:
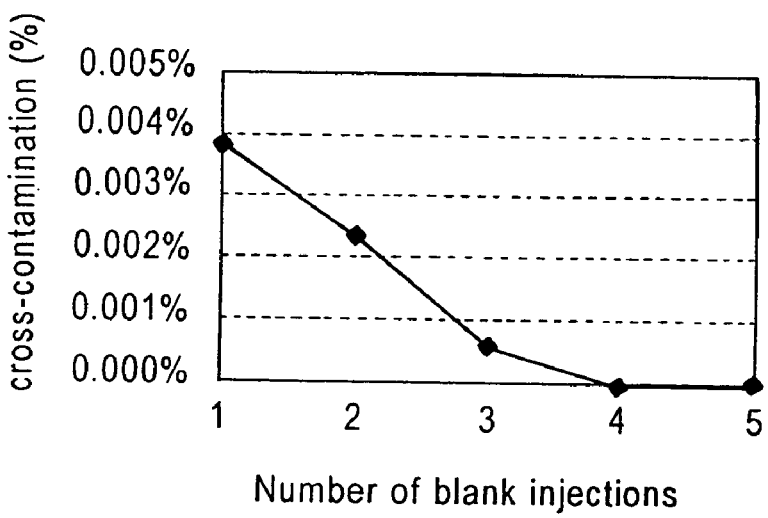
Figure 4A:
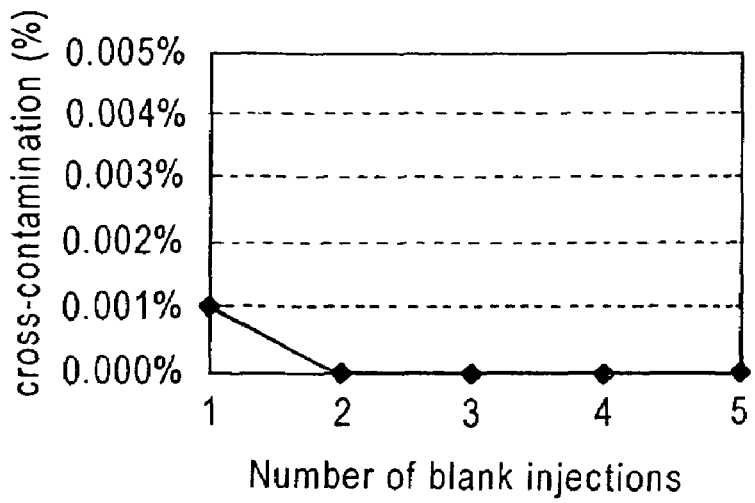
FIGS. 4(A) to 4(C) are charts showing an effect of reducing cross-contamination in a case of a needle having a surface coated with platinum plating and polished.
Figure 4B:
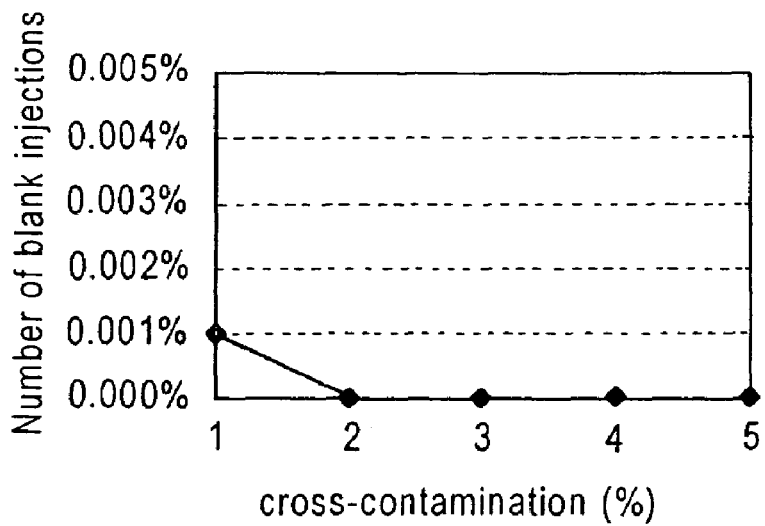
Figure 4C:
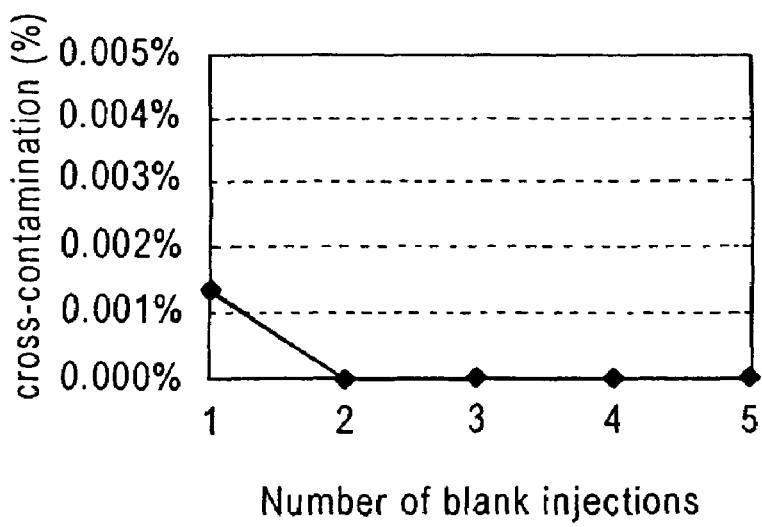

FIGS. 3(A) to 3(C) are charts showing an effect of reducing cross-contamination in a case of the needle having the surface coated with platinum plating (comparative example). The needle is coated with platinum plating with the method disclosed in Patent Document 1. FIGS. 4(A) to 4(C) are charts showing an effect of reducing cross-contamination in a case that the surface of the needle 7 shown in FIGS. 3(A) to 3(C) is polished with the mechanical polishing (embodiment).

The comparative example had the average roughness Ra of 45.42 nm and the average roughness Rtm of the ten points of maximum roughness of 278.89 nm. The embodiment had the average roughness Ra of 10.14 nm and the average roughness Rtm of the ten points of maximum roughness of 101.43 nm.

In this experiment, strong alkaline chlorhexidine hydrochlorate was diluted in mobile phase liquid as a sample. A peak area A of the sample was obtained first. Then, only the mobile phase liquid (blank sample) was injected and a peak area B at the same holding time was measured. An extent of cross-contamination was measured as a ratio C (%) of B over A. The tests were repeated three times. In the charts, the horizontal axis represents the number of injections of blank solution, and the vertical axis represents the cross-contamination (%).

As shown in FIGS. 3(A) to 3(C) and FIGS. 4(A) to 4(C), in the case of the needle polished with the mechanical polishing, the cross-contamination in the first round of injection of the blank sample becomes smaller. Further, in the case of the needle without polishing, it was necessary to repeat the injection of the blank sample four or more times to reach a detection limit, whereas two blank injections were sufficient for the polished needle.

Accordingly, when the needle surface is coated with the coating material having a chemical activity smaller than the parent material and polished to reduce the surface roughness, it is possible to suppress the cross-contamination as compared with the case that the surface is coated only.

In the experiment, conditions of the liquid chromatograph are as follows.

Mobile phase: 100 mM phosphoric acid buffer containing perchloricacid (pH 2.6)/acetonitrile=55/45
Flow rate: 0.2 mL/min
Column: VP-ODS, diameter 2 mm, length 150 mm
Column oven temperature: 40° C.
Detector: UV 260 nm
Sample: chlorhexidine hydrochlorate 12 mg/10 mL mobile phase
Sample injection amount: 2 μL In the comparative sample, the surface of the needle 7 was plated with platinum. A substantially same effect can be obtained by applying the present invention in a case that the needle is coated with PEEK or a synthetic resin film, and the needle is formed of a parent material other than stainless steel. The parent material and coating material are not limited to the embodiments. For example, a substantially same effect as with platinum can be obtained when the needle is plated with precious metals such as other platinum family elements or gold instead of platinum.

The dimensions of the needle 7 in the embodiments are just one example, and the present invention is not limited thereto. The surface roughness is not limited to that in the embodiment, and the average roughness Ra may be about 10 to 20 nm.

The present invention is generally applicable to auto-samplers in which liquid samples are successively collected from plural vials through a needle. The present invention is also applicable to auto-samplers of various analytical devices for analyzing liquid samples as well as the auto-sampler of liquid chromatograph.

The disclosure of Japanese Patent Application No. 2004-100328 filed on Mar. 30, 2004 is incorporated in the application.

While the invention has been explained with reference to the specific embodiments of the invention, the explanation is illustrative and the invention is limited only by the appended claims.

What is claimed is:

1. A method of forming a needle for an auto-sampler successively collecting liquid samples from plural sample containers, comprising:

coating a parent material forming the needle with a coating material having a thickness of several micrometers, said coating material having a chemical activity small than that of the needle, and polishing said coated parent material so that a surface has an average roughness of 10 to 20 nm, said coated parent material being polished by mechanical polishing with abrasive grains affixed to a polishing cloth.

2. A method of forming a needle according to claim 1, wherein said coating material includes a precious metal.

3. A method of forming a needle according to claim 1, wherein said coating material includes a synthetic resin.

4. A method of forming a needle according to claim 1, wherein said coating material includes quartz.

5. A method of forming a needle according to claim 1, wherein said coating material is polished to have a thickness greater than the average roughness.

6. A method of forming a needle according to claim 1, wherein said coating material is polished to have a polished surface with an average roughness of 10 points of maximum roughness with about 101.43 nm.

7. A method of forming a needle according to claim 1, wherein said coated parent material is polished by hand with the abrasive grains affixed to the polishing cloth.

8. A method of forming a needle for an auto-sampler successively collecting liquid samples from plural sample containers, comprising:

coating a coating material having a chemical activity small than that of the needle on an outer surface of the needle to have a thickness of several micrometers, and polishing said outer surface of the coating material so that the outer surface has an average roughness of 10 to 20 nm by mechanical polishing with abrasive grains affixed to a polishing cloth, wherein said coating material is selected from the group consisting of a precious metal, synthetic resin and quartz.

\* \* \* \* \*